United States Patent [19]

Peterson

[11] Patent Number: 4,617,265

[45] Date of Patent: Oct. 14, 1986

[54] COLONY BLOT ASSAY FOR ENTEROTOXIGENIC BACTERIA

[75] Inventor: Johnny W. Peterson, Dickinson, Tex.

[73] Assignee: Board of Regents, University of Texas System, Austin, Tex.

[21] Appl. No.: 652,369

[22] Filed: Sep. 19, 1984

[51] Int. Cl.[4] .................... C12Q 1/10; G01N 53/00
[52] U.S. Cl. .................................. 435/38; 435/7; 435/805; 436/530
[58] Field of Search ............... 435/4, 7, 30, 34, 38, 435/39, 28, 805; 436/530, 531

[56] References Cited

U.S. PATENT DOCUMENTS

| | | | |
|---|---|---|---|
| 4,002,532 | 1/1977 | Weltman et al. | 435/7 |
| 4,343,896 | 8/1982 | Wolters et al. | 435/810 |
| 4,399,229 | 8/1983 | Kelton et al. | 436/519 |
| 4,407,943 | 10/1983 | Cole et al. | 435/7 |
| 4,446,232 | 5/1984 | Lidtta | 435/805 |

FOREIGN PATENT DOCUMENTS

| | | |
|---|---|---|
| 0108303 | 5/1984 | European Pat. Off. |
| 0109012 | 5/1984 | European Pat. Off. |
| 85/02611 | 6/1985 | PCT Int'l Appl. |

OTHER PUBLICATIONS

Beutin, et al., J. Clin. Microbiol., vol. 19, No. 3, pp. 371-375 (Mar. 1984).
Sen, et al., J. Clin. Microbiol., vol. 19, No. 2, pp. 194-196 (Feb. 1984).
Svennerholm, et al., J. Clin. Microbiol., vol. 17, No. 4, pp. 596-600 (Apr. 1983).
Germani, et al., (1984), Ann. Microbiol., 135: 297-310, (Chem. Abstracts; vol. 102, No. 126725h).
Lloyd, (1983), Inst. Natl. Sarte Recl. Med., 144: 555, (Chem. Abstracts, vol. 101, No. 6897a).
Yolken, et al, Journal of Clinical Microbiology, vol. 6, 1977, pp. 439-444.
Grunstein, et al, Proceedings of the National Academy of Sciences U.S.A., vol. 72, No. 10, 1975, pp. 3961-3965.
The Microbiol. World, 4th ed. 1976, Prentice-Hall Inc., Englewood Cliffs, N.J., p. 435.
DIFCO Manual 9th ed., 1977, Difco Laboratories Inc., Detroit, Mich., 48201 pp. 88-89 and 130.
Bramucci, et al, J. Clinical Microbiology, 1978, vol. 8, No. 2, pp. 252-255.
Mekalanos, et al., Proceedings of the National Academy of Sciences, 1978, vol. 75, No. 2, pp. 941-945.

*Primary Examiner*—Sidney Marantz
*Assistant Examiner*—William J. Herald
*Attorney, Agent, or Firm*—Arnold, White & Durkee

[57] ABSTRACT

A plate of suitable nutrient medium and agar is inoculated with bacteria from a biological sample. Bacterial colonies are cultured on the plate and are then overlaid with a soft agar layer containing bacterial lysing agents. A removable sheet with bound first animal antibodies for cholera toxin is used to contact the overlaid lysed colonies. The sheet is then exposed to a second animal antibody to cholera toxin followed by treatment with a third animal antibody against the second animal antibody, said third animal antibody being coupled to an enzyme capable of generating a chromophoric product. The sheet is then developed by immersion in a substrate and system for the bound enzyme to produce chromophoric products at the sites of enterotoxigenic bacterial colonies.

16 Claims, No Drawings

COLONY BLOT ASSAY FOR ENTEROTOXIGENIC BACTERIA

BACKGROUND OF THE INVENTION

The present invention relates specifically, but not by way of limitation, to an effective method for readily detecting the presence of enterotoxigenic bacteria in biological samples. Presently, methods available in the clinical laboratory for detection of enterotoxigenic bacteria are cumbersome, time consuming, often impractical for effective diagnostic usage.

Enterotoxigenic bacteria, most commonly strains of enterotoxigenic *Escherichia coli*, are a major cause of diarrheal disease. Such enterotoxigenic *E. coli* strains elaborate at least two toxins, one of which is heat-labile and is immunologically related to the enterotoxin of Vibrio cholerae in that antibody to the V. cholerae enterotoxin cross-reacts with the heat-labile *E. coli* enterotoxin (see e.g. Yolken et al., J. Clin. Microbiol., pp 439–444, Nov. 1977).

The present invention comprises a series of readily performed steps to elucidate the presence in biological samples of enterotoxigenic *E. coli* producing heat-labile enterotoxin. Said steps provide a method utilizable in hospital laboratories for rapid diagnoses in the aid of effective treatment of diarrheal disease. While it is acknowledged that the individual steps of the present invention are representative of procedures known to those skilled in the art, the unique combination of said steps in the manner prescribed herein presents a significant technological advance in this field of medicine.

SUMMARY OF THE INVENTION

Enterotoxigenic *Escherichia coli* are detected in a biological sample by a series of steps. Sterile plates comprising agar and a suitable nutrient medium are inoculated with a portion of the biological sample. The inoculated plates are incubated to facilitate growth of bacterial colonies thereupon. The bacterial colony-containing plate is then overlaid with a soft agar layer comprising bacterial lysing agents to produce overlaid lysed bacterial colonies. The overlaid lysed bacterial colonies are then contacted with a removable sheet comprising a bound first animal antibody for cholera toxin. The sheet is then removed, washed, and exposed to a second animal antibody for cholera toxin. The exposed sheet is washed and treated with a third animal antibody against the second animal antibody, said third animal antibody being coupled to an enzyme capable of generating a chromophoric product. The sheet is then washed and developed by immersion with a substrate for the enzyme to produce chromorphoric products at the site of bound coupled enzyme.

DESCRIPTION OF THE PREFERRED EMBODIMENT

Nitrocellulose sheets having a diameter of about 82 mm were incubated overnight with agitation at 25° C. in a 1:800 dilution of burro antiserum specific for cholera toxin in TBS. Different antisera may require different dilutions for optimal effectiveness. The sheets were then washed briefly in Tris buffered saline (TBS, 29.24 g NaCl/liter, 2.42 g Tris/l, adjusted to pH 7.5 with HCl) before incubation in a TBS solution containing 3 g gelatin per 100 ml for 1 hour at 25° C. The treated nitrocellulose sheets were then briefly washed with pH 7.4 tris buffer and gently blotted between pieces of Whatman filter paper as a final preparation for usage. While nitrocellulose sheets are preferable in the practice of the invention, other materials such as Nylon may be used instead A portion of the biological sample, fecal material in this particular case, was inoculated onto a sterile blood agar plate or Petri dish of about 100 mm diameter and incubated at about 37° C. for about 18 to 24 hours to result in the appearance of bacterial colonies. Each plate with bacterial colonies thereupon was inverted for about 30 min over a 7 cm filter paper disc saturated with about 1 ml chloroform. This chloroform vapor treatment, while preferred to aid in biological containment and possible lysing, is not thought essential to the function of the present invention.

A soft agar solution comprising 1 g Difco tryptone, 0.8 g Difco agar, 0.8 g sodium chloride and 100 ml water was sterilized and cooled to about 45° C. Each colony-containing plate was removed from over the chloroform disc and overlaid with a soft agar solution comprising 3 ml of the above-described 45° C. soft agar solution also containing the bacterial lysing agents sodium dodecyl sulfate (200 ul of a 5 mg/ml aqueous solution) and lysozyme (Sigma Chemical Co., 200 ul of a 25 mg/ml TBS solution). The agar overlay was allowed to solidify for about 5 min at at about 25° C.

The solidified agar overlay in each colony-containing plate was then contacted with a treated nitrocellulose sheet (82 mm disc) and air bubbles between the sheet and soft agar removed by gentle pressing with a gloved finger. After at least about a 1 hr incubation at ambient temperature, the 82 mm discs were removed with forceps and washed with TBS for at least one 10 min time interval. The washed sheets or discs were then exposed to a second animal antibody against cholera toxin for about 1 hr at 25° C. This second animal antibody was specifically purified rabbit antibody against cholera toxin diluted 1:6000 in AB buffer (100 ml TBS containing about 1 g gelatin). The exposed sheets or discs were then washed twice in TBS buffer for ten minute periods.

The washed nitrocellulose discs or sheets were then treated with a third animal antibody against the second animal antibody earlier utilized herein and coupled to an enzyme. The third animal antibody was goat antiserum to rabbit IgG and was conjugated to horseradish peroxidase. The goat antiserum was in a 1:3000 dilution with AB buffer and the treatment comprised an incubation of the sheets in said dilution for about 1 hr at about 25° C. The sheets were then removed and washed twice in TBS for about 10 min intervals.

The washed nitrocellulose discs or sheets were then developed at 25° C. by immersion in a substrate solution comprising: 60 ul $H_2O_2$; 60 mg Redox indicator (alphanapthol reagent dissolved in cold methanol); and 100 ml TBS. This system represents a preferred manner of producing chromophoric (visually observable color-containing) products with the horseradish peroxidase enzyme. When purplish spots on the nitrocellulose sheets had satisfactorily developed (usually within about 10 min) the nitrocellulose sheets were washed in a water bath, dried and preserved between plastic sheets. The purplish spots appearing on the nitrocellulose sheets are indicative of proximity to enterotoxigenic bacterial colonies, said enterotoxins being liberated by bacterial lysis and diffusing through the soft agar to bind to the first animal antibody against cholera toxin affixed to the sheet of nitrocellulose. The second animal antibody to cholera toxin served to generate a new molecular "handle" to the bound bacterial cholera-like enterotoxin. The horseradish peroxidase conjugated third antibody, binding to the bound second animal antibody served to anchor a chromophore generating enzyme to the bound second animal antibody, said enzyme being only one of many possible markers being well known to those skilled in the art.

The particular animal species i.e. burro; rabbit and goat utilized in the above embodiment are not meant to be limiting as there are numerous obvious antibody combinations and permutations which could be designed by following the prescriptions of the present invention to confer the same specificity to the assay procedure. The rabbit antibody, however, purified by immunoaffinity chromatography on cholera toxin bound to a chromotographic matrix is important to the function of the present invention.

The biological samples, while preferably fecal material from man or domestic animals, may also be water samples, food samples or other potentially enterotoxic bacteria-containing materials.

The process described herein is also applicable to genetic recombinant work where recombinant bacteria producing cholera-like or enterotoxigenic toxins are sought.

A Transblot kit from Bio-Rad Laboratories (Richmond, Calif. 94804) was utilized herein to provide goat antiserum conjugated to horseradish peroxidase and the alpha napthol redox indicator.

The above described tests were also similarly applied to isolates of about 100 strains of *E. coli* independently characterized as to their enterotoxigenicity instead of unknown biological samples. About 80% of the strains characterized as enterotoxigenic by bio-assays were found to be enterotoxigenic by the process of the present invention. No false positive testing results were found.

Changes may be made in the construction, operation and arrangement of the various segments, elements, steps and procedures described herein without departing from the inherent concept and scope of the invention as defined in the following claims.

I claim:

1. A process for detecting enterotoxigenic *Escherichia coli* which produces a toxin having cross-reactivity with antibody for *Vibrio cholerae* toxin in a biological sample comprising:

obtaining a biological sample;

inoculating a sterile plate comprising nutrient medium and agar with a portion of said biological sample;

incubating the inoculated plate to facilitate growth of bacterial colonies thereupon;

overlaying the bacterial colony-containing plate with a soft agar layer comprising bacterial lysing agents to produce overlaid lysed bacterial colonies;

contacting the soft agar layer with a removable sheet comprising a bound first animal antibody for cholera toxin;

removing and washing said sheet;

exposing said washed sheet to a second animal antibody for cholera toxin;

washing said exposed sheet treating said washed exposed sheet with a third animal antibody against the second animal antibody, said third animal antibody being coupled to an enzyme capable of generating a chromophoric product;

washing said treated sheet; and developing the sheet by immersion with a substrate for the bound enzyme to produce chromophoric product.

2. The process of claim 1 wherein the sterile plate is defined further as comprising a Petri dish.

3. The process of claim 1 wherein the nutrient medium is defined further as comprising blood agar.

4. The process of claim 1 wherein the nutrient medium is defined further as comprising MacConkey agar.

5. The process of claim 1 wherein the nutrient medium is defined further as comprising SS(Hektoen) agar.

6. The process of claim 1 wherein the biological sample is defined further as being fecal material.

7. The process of claim 1 wherein the biological sample is defined further as being water.

8. The process of claim 1 wherein the soft agar is defined further as comprising about 0.8% agar and about 0.8% sodium chloride.

9. The process of claim 8 wherein the soft agar is defined further as being at about 45° C. and as comprising about 0.033 percent sodium dodecyl sulfate and about 0.167 percent lysozyme.

10. The process of claim 1 wherein the removable sheet is defined further as comprising nitrocellulose.

11. The process of claim 1 wherein the bound first animal antibody is defined further as being an antiserum.

12. The process of claim 12 wherein the antiserum is defined further as being burro antiserum.

13. The process of claim 1 wherein the second animal antibody is defined further as being rabbit IgG and as being purified by immunoaffinity chromotagraphy on a chromatographic matrix comprising cholera toxin.

14. The process of claim 1 wherein the third animal antibody is defined further as being a goat immunoglobulin.

15. The process of claim 1 wherein the substrate is defined further as comprising hydrogen peroxide and the immersion is defined further as also being with an alpha naphthol redox indicator.

16. The process of claim 1 wherein an additional step of exposing the bacterial colonies to chloroform vapors is applied immediately before overlaying with soft agar.

* * * * *